United States Patent
Liu et al.

(10) Patent No.: US 12,029,737 B2
(45) Date of Patent: Jul. 9, 2024

(54) AUTOIMMUNE THERAPY

(71) Applicant: LDN Pharma Limited, England (GB)

(72) Inventors: Wai Liu, London (GB); Angus Dalgleish, London (GB)

(73) Assignee: LDN Pharma Limited, London (GB)

( * ) Notice: Subject to any disclaimer, the term of this patent is extended or adjusted under 35 U.S.C. 154(b) by 277 days.

(21) Appl. No.: 17/042,904

(22) PCT Filed: Mar. 29, 2019

(86) PCT No.: PCT/GB2019/050937
§ 371 (c)(1),
(2) Date: Sep. 28, 2020

(87) PCT Pub. No.: WO2019/186207
PCT Pub. Date: Oct. 3, 2019

(65) Prior Publication Data
US 2021/0052574 A1    Feb. 25, 2021

(30) Foreign Application Priority Data
Mar. 29, 2018  (GB) ..................... 1805207

(51) Int. Cl.
*A61K 31/485*  (2006.01)
*A61K 31/59*   (2006.01)
*A61P 5/14*    (2006.01)
*A61P 37/06*   (2006.01)

(52) U.S. Cl.
CPC ............ *A61K 31/485* (2013.01); *A61K 31/59* (2013.01); *A61P 5/14* (2018.01); *A61P 37/06* (2018.01)

(58) Field of Classification Search
CPC .............................. A61K 31/485; A61K 31/59
See application file for complete search history.

(56) References Cited

FOREIGN PATENT DOCUMENTS

WO   2017/141104 A2    8/2017
WO   WO-2017141104 A2 *  8/2017  ............. A61K 31/17

OTHER PUBLICATIONS

Hu et al., "Pseuo-hyperthroidism in a multiple sclerosis patient taking high-dose biotin," Multiple Sclerosis Journal, vol. 24, No. Suppl. 1, Feb. 1, 2018, pp. 45 (Year: 2018).*
Webpage printout of https://www.woodlandhillspharmacy.com/low-dose-naltrexone-psoriasis/, first published Dec. 6, 2017, pp. 1-4. (Year: 2017).*
Webpage printout of Code for view-source:https://www.woodlandhillspharmacy.com/low-dose-naltrexone-psoriasis/, accessed Jul. 1, 2022, pp. 1-4. (Year: 2022).*
Metze et al., J Am Acad Dermatol, Oct. 1999, pp. 533-539.*
Metze et al., J Am Acad Dermatol, Oct. 1999, pp. 533-539. (Year: 1999).*
Shear, NH. Oral Calcitriol for Psoriasis, Aug. 1, 1996, pp. 1-4. (Year: 1996).*
Dalgleish, A.G., "Vitamin D may be vital for the efficacy of low-dose naltrexone (LDN)," www.phoenixrising.me, URL:https://forums.phoenixrising.me/threads/vitamin-d-may-be-vital-for-the-efficacy-of-low-dose-naltrexone-Idn.52487, Jul. 4, 2019.
Hooper et al., "Replies o: Request or Information: Solicit Input for New Research Strategies for Malgic Encephalomlitis/Chronic Fatigue Syndrome (ME/CFS) Notice No. NOTNS16024," URL: htps://www.nih.gov/sites/efault/files/research-training/initiaties/mefs/rfi-healthcare-professionals-researchers.pd, pp. 1-111, 2017.
Hu et al., "Pseuo-hyperthroidism in a multiple sclerosis patient taking high-dose biotin," Multiple Sclerosis Journal, vol. 24, No. Suppl. 1, Feb. 1, 2018, pp. 45.
Gunster, Marco, International Search Report and Written Opinion, European Patent Office, PCT/GB2019/050937, 2019.

* cited by examiner

*Primary Examiner* — Craig D Ricci
*Assistant Examiner* — Janet L Coppins
(74) *Attorney, Agent, or Firm* — Gavrilovich, Dodd & Lindsey LLP

(57) ABSTRACT

The present invention relates to naltrexone or an analogue thereof, wherein the analogue is methylnaltrexone, naloxone, nalmefene and nalorphine and vitamin D or an active metabolite, or a pharmaceutically acceptable salt of either for separate, sequential or simultaneous administration, for use in the therapy of an autoimmune disease.

5 Claims, No Drawings

AUTOIMMUNE THERAPY

CROSS REFERENCE TO RELATED APPLICATIONS

This application is a U.S. National Stage Application filed under 35 U.S.C. § 371 and claims priority from International Application No. PCT/GB2019/050937, filed Mar. 29, 2019, which application claims the benefit of Great Britain Patent Application No. 1805207.6, filed Mar. 29, 2018, the disclosures of which are incorporated herein in their entirety by reference.

FIELD OF INVENTION

This invention relates to regimes of drug administration and drug combinations for the treatment of autoimmune diseases.

BACKGROUND OF THE INVENTION

Autoimmune diseases are a broad spectrum of disorders characterised by the abnormal recognition and reaction to self-antigens by the immune system. Pathologically, autoimmune diseases can be caused by genetic factors, environmental factors, infectious agents or a combination of any number of the above. Different autoimmune diseases can be systemic, such as systemic lupus erythematosus or localised to particular regions of the body, such as dermatitis.

There are now more than 80 recognised autoimmune diseases, with a steady rise in the prevalence of diagnosis being reported in Western societies. The reason for the increase is unknown, but is thought to be linked to increasing urbanisation and the subsequent increase in exposure to environmental factors linked to the onset of autoimmune diseases. Moreover, higher levels of stress have been linked to the onset of particular autoimmune diseases, as has a largely sedentary lifestyle, generally suggesting that autoimmune diseases are a symptom of modern life.

One example of a well-known autoimmune disease is multiple sclerosis (MS). MS is a neurological disease where damage to neuronal myelin sheaths leads to impaired neuronal communication and the onset of a variety of neurological defects such as motor-sensory impairment and psychiatric issues. Like many other autoimmune diseases, the exact underlying cause of MS is unknown, but is thought to arise via a combination of genetic mutations that increase the risk of developing the disease, and increased exposure to certain environmental and infectious agents. As with the majority of autoimmune diseases, genetic risk factors only increase the predisposition of the subject towards developing MS, but the disease can still manifest in the absence of genetic mutations.

Another example of autoimmune disease is psoriasis. Psoriasis is a condition characterised by localised inflamed pruritic patches on the skin that cause significant discomfort to the subject. The underlying mechanism of psoriasis is unknown, but is thought to be exacerbated by hyperactive skin renewal mechanisms. It is possible that particular genetic signatures increase the risk of developing the disease, as psoriasis can be hereditary. Genetic and environmental factors are thought to interfere with the normal immune response by increasing self-recognition of healthy skin by invading T-cells. The destruction of healthy skin by the immune system induces the deepest layer of skin to accelerate the production of new skin, leading to the generation of the pruritic patches that characterise psoriasis.

Another type of autoimmune disease is thyroiditis, which is characterised by swelling (inflammation) of the thyroid gland. It causes either unusually high or low levels of thyroid hormones in the blood. One particular type of thyroiditis is called Hashimoto's disease, in which the immune system turns against the body's own tissues and attacks the thyroid. This can lead to hypothyroidism, a condition in which the thyroid does not make enough hormones for the body's needs, leading to tiredness, weight gain and dry skin and a lump to form in the throat.

As the underlying causes of many autoimmune diseases remain elusive, the development of preventative measures to combat the onset of many autoimmune diseases is unattainable. There is thus a need to develop curative therapies. Moreover, the link between lifestyle factors and the increasing frequency of diagnosis has created an even greater urgency for developing effective treatments that can reverse or bring under control the symptoms of autoimmune diseases.

SUMMARY OF THE INVENTION

According to a first aspect of the invention, there is provided naltrexone or an analogue thereof, wherein the analogue is methylnaltrexone, naloxone, nalmefene and nalorphine, and vitamin D or an active metabolite thereof or a pharmaceutically acceptable salt of either, as a combined preparation for simultaneous, sequential, or separate use in the therapy of autoimmune diseases.

According to a second aspect of the invention, there is provided a pharmaceutical composition comprising naltrexone or an analogue thereof, wherein the analogue is methylnaltrexone, naloxone, nalmefene and nalorphine, in a combined formulation with vitamin D or an active metabolite or a pharmaceutically acceptable salt of either. The pharmaceutical composition may be for use in the first aspect of the invention.

In a third aspect of the invention, there is provided a method for the treatment of an autoimmune disease, comprising administering to a subject in need thereof a therapeutically effective amount of naltrexone or an analogue thereof, wherein the analogue is methylnaltrexone, naloxone, nalmefene and nalorphine, and vitamin D or an active metabolite or a pharmaceutically acceptable salt of either, wherein said naltrexone products and said vitamin D product are administered separately, sequentially or simultaneously.

DETAILED DESCRIPTION OF THE INVENTION

The present invention is based on the realisation that naltrexone together with vitamin D has a synergistic effect in the treatment of autoimmune diseases. The inventors have found that the therapeutic pathways of naltrexone and vitamin D interact in such a way that enhances the therapeutic effect when used in combination. Moreover, the enhancement in efficacy of the dual therapy is significantly greater than what would be expected through simple additive effects observed when both are administered in isolation. As such, the present invention provides an effective treatment to alleviate symptoms associated with autoimmune diseases, in particular psoriasis.

The invention is herein defined with respect to the following terms.

As used herein "naltrexone" refers to morphinan-6-one, 17-(cyclopropylmethyl)-4,5-epoxy-3,14-dihydroxy-(5α) having the above chemical structure, and pharmaceutically acceptable salts, solvates, hydrates, stereoisomers, clathrates, metabolites and prodrugs thereof. The use of naloxone, a structural analogue of naltrexone, is within the scope of the invention and is encompassed within the term "analogue" used in the description and the claims. Similarly, methylnaltrexone, nalmefene and nalorphine, are envisaged as suitable analogues for use in all aspects of the invention. 6-ß naltrexol (17-(Cyclopropylmethyl)-4,5-epoxymorphinan-3,6beta,14-triol) is envisaged as a particularly suitable metabolite of naltrexone. The preferred form of naltrexone is as its hydrochloride salt form. Preferably the naltrexone is to be administered in a low dose regime, i.e. as "low dose naltrexone", (LDN) where the naltrexone, analogue or metabolite is administered at a dose less than 0.5 mg/kg, preferably less than 0.2 mg/kg, more preferably between 0.01 mg/kg and 0.08 mg/kg.

As used herein, "vitamin D" refers to a group of fat soluble secosteroids that aid the absorption of calcium, magnesium, phosphate, iron and zinc from the gut. Vitamin D can be administered through topical ointments, dietary supplements, pharmaceutical compositions, or the production of vitamin D can be stimulated within a subject through exposure to natural or artificial sunlight (phototherapy).

As used herein, the terms "therapy" and "treating" and "treatment" and "to treat" refer to both 1) therapeutic measures that cure, slow down, and/or halt progression of a diagnosed pathologic condition or disorder and 2) prophylactic or preventative measures that prevent and/or slow the development of a targeted pathologic condition or disorder. Thus, those in need of treatment include those already with the disorder; those prone to have the disorder; and those in whom the disorder is to be prevented. In some instances, a subject is successfully "treated" for an autoimmune disease according to the novel applications of the present invention if the patient shows one or more of the following: for example, a reduction in swelling, pruritus, fatigue, general malaise, fever, skin lesions, hair loss or weight loss. In some instances treatment may result in halting the further progression of symptoms of the disorder or the emergence of symptoms of the disorder.

As used herein, the term "subject" refers to any animal (e.g., a mammal), including, but not limited to, humans, non-human primates, canines, felines, rodents, and the like, which is to be the recipient of a particular treatment. Typically, the terms "subject" and "patient" are used interchangeably herein in reference to a human subject.

In the context of vitamin D, an "active metabolite" means any intermediate or product derived from a vitamin D metabolic pathway that participates in the therapeutic mechanism of the invention. For example, metabolite may refer to a vitamin D precursor which can be incorporated into a vitamin D synthetic pathway naturally occurring within the subject to undergo therapy. Alternatively, metabolite may refer to a molecule derived from an anabolic or catabolic process that directly or indirectly utilizes vitamin D. Non-limiting examples of vitamin D metabolites include ergocalciferol, cholecalciferol, calcidiol, and calcitriol, 1a-hydroxycholecalciferol, 25-hydroxycholecalciferol, 1a,25-hydroxycholecalciferol, 24,25hydroxycholecalciferol. Dosage regimes of vitamin D and metabolites thereof are well described in the art and will as such be readily known to those skilled in the art.

As used herein, the terms "concurrent administration" or "concurrently" or "simultaneous" mean that the naltrexone/ low dose naltrexone, analogue or metabolite, wherein the analogue is methylnaltrexone, naloxone, nalmefene and nalorphine and the vitamin D or metabolite thereof are administered as part of the same treatment regimen.

"Simultaneous" administration, as defined herein, includes the administration of the two active components within about 2 hours or about 1 hour or less of each other, even more preferably at the same time.

"Separate" administration, as defined herein, includes the administration of the two active components within a 24 hour period, more than about 12 hours, or about 8 hours, or about 6 hours or about 4 hours or about 2 hours apart.

"Sequential" administration, as defined herein, includes the administration of the two active components in multiple aliquots and/or doses and/or on separate occasions. The naltrexone product may be administered to the patient before and/or after administration of the vitamin D product. Alternatively, the naltrexone product is continued to be applied to the patient after treatment with the vitamin D product.

Preferably, the two active components are to be administered simultaneously. "Biological sample", as defined herein, includes samples obtained from a patient or subject, which may comprise blood, plasma, serum, urine, saliva or sputum.

According to a first aspect of the invention, there is provided naltrexone or an analogue thereof, wherein the analogue is methylnaltrexone, naloxone, nalmefene and nalorphine, and vitamin D or an active metabolite or a pharmaceutically acceptable salt of either, as a combined preparation for simultaneous, sequential, or separate use in the therapy of an autoimmune disease.

In certain embodiments, the vitamin D product is to be administered to the patient in an amount sufficient to bring the subject's blood vitamin D concentration to at least 40 ng/ml, more preferable at least 50 ng/ml. Preferably, the blood vitamin D concentration is raised to within a range of from 40 to 120 ng/ml, more preferably the blood vitamin D concentration is raised to within a range of from 40 to 90 ng/ml.

A sufficient amount can be determined by the skilled person by making a routine assessment of certain parameters of the patient to undergo the administration, such as, but not limited to, age, weight, gender, history of illness and/or other lifestyle factors including smoking, alcohol consumption and the level of exercise. Furthermore the skilled person can ascertain whether a dose has been sufficient to raise the vitamin D blood concentration to a sufficient amount by performing routine biochemical and analytical assays on a biological sample obtained from the subject. Preferably, the sample upon which said analysis is to be performed is blood. Examples of such well known assays include but are not limited to mass spectrometry, where the level of vitamin D or active metabolites thereof can be quantitatively measured. A sufficient amount is therefore an amount that achieves the desired blood vitamin D concentration. The desired concentration can be achieved after single administration or after repeated administrations of a dose of vitamin D or an active metabolite thereof. Where the vitamin D product and the naltrexone product are to be administered simultaneously, it is immaterial whether the vitamin D blood concentration is within the desired range prior to administration of the naltrexone product, provided that the vitamin D product is administered in an amount sufficient to raise the blood vitamin D concentration to within the desired concentration range. Other methods for determining the concentration of vitamin D or active metabolites thereof within a biological sample obtained from the patient will be well known to the skilled person, for example, by using standard serum tests or the SpectraCell test (SpectraCell Laboratories, Inc., Dallas, Texas). In certain embodiments, the amount of the vitamin D sufficient to raise the blood vitamin D concentration to beyond a certain level is referred to as the "therapeutically effective amount" of the vitamin D product.

In another embodiment, the naltrexone product and the vitamin D product are for simultaneous administration. The naltrexone and vitamin D products may be provided as a combined preparation, where the vitamin D product may be provided in a crystalline or amorphous form. The combined preparation will be provided in a form that is acceptable, tolerable, and effective for the subject. Numerous pharmaceutical forms and formulations for biologically active agents are known in the art, and any and all of these are contemplated by the present invention. For example, the combined preparation may be formulated in an oral solution, a caplet, a capsule, an injectable, an infusible, a suppository, a lozenge, a tablet, a cream or salve or an alternative topical ointment and the like.

In another embodiment, the naltrexone product is to be administered to the subject separately from the vitamin D product. The naltrexone product may be administered after the administration of the vitamin D product, such that the vitamin D is within the desired blood concentration when the naltrexone product is administered. Preferably, the desired blood concentration is at least 40 ng/ml, more preferably the desired blood concentration is at least 50 ng/ml. More preferably, the naltrexone product is to be administered to the subject such that the blood vitamin D concentration is raised to within a range of from 40 to 120 ng/ml, more preferably to within a range of from 40 ng/ml to 90 ng/ml. The blood concentration of vitamin D or any active metabolite thereof can be determined from within a biological sample obtained from the subject by any of the methods described above.

In another embodiment, the naltrexone or an analogue thereof, wherein the analogue is methylnaltrexone, naloxone, nalmefene and nalorphine or a pharmaceutically acceptable salt is administered as low dose naltrexone, i.e. at a dose less than 0.5 mg/kg, preferably less than 0.2 mg/kg, more preferably between 0.01 mg/kg and 0.08 mg/kg.

In another embodiment, the vitamin D or analogue thereof, or pharmaceutically acceptable salt of either is administered at a daily dose in the range of about 400 IU to about 10,000 IU per dosage form, preferably in the range of about 2,000 to about 8,000, more preferably in the range of about 3,000 to 7,000.

In another embodiment, the autoimmune disease for treatment is selected from the list consisting of hepatitis, ankylosing spondylitis, Lyme disease, systemic lupus erythematosus (SLE), fibromyalgia, myasthenia gravis, Guillain-Barré syndrome, multiple sclerosis, Behçet's disease, chronic fatigue syndrome, psoriasis or thyroiditis, such as hashimotos thyroiditis. Preferably, the autoimmune disease is psoriasis, SLE or thyroiditis, preferably SLE or thyroiditis.

In another embodiment, the naltrexone and vitamin D may be administered in combination with other known therapies for autoimmune diseases. Introducing this combination of naltrexone and vitamin D is shown to increase the therapeutic effect of the known therapy. For example, the combination significantly improves the effectiveness of thyroid supplementation therapy such as using a porcine product.

According to a second aspect of the invention, there is provided a pharmaceutical composition comprising naltrexone or an analogue thereof, wherein the analogue is methylnaltrexone, naloxone, nalmefene and nalorphine in a combined formulation with vitamin D or an active metabolite or a pharmaceutically acceptable salt of either. The pharmaceutical composition may be provided as an oral solution, a caplet, a capsule, an injectable, an infusible, a suppository, a lozenge, a tablet, a cream or salve or an alternative topical ointment and the like. In certain embodiments, the pharmaceutical composition is provided in oral dosage forms, particularly as a tablet.

As used herein the term "pharmaceutical composition" means, for example, a mixture containing a specified amount of a therapeutic compound or compounds, e.g. a therapeutically effective amount, in a pharmaceutically acceptable carrier to be administered to a mammal, e.g., a human in order to treat a disease.

As used herein the term "pharmaceutically acceptable" refers to those compounds, materials, compositions and/or dosage forms, which are, within the scope of sound medical judgment, suitable for contact with the tissues of mammals, especially humans, without excessive toxicity, irritation, allergic response and other problem complications commensurate with a reasonable benefit/risk ratio.

The term formulation is intended to include the mixture of the active component(s) with encapsulating material as a carrier providing a solid dosage form in which the active compound (with or without other carriers) is surrounded by a carrier which is thus in association with it. Similarly, cachets are included. Tablets, powders, cachets, and capsules can be used as solid dosage forms suitable for oral administration.

The pharmaceutical formulation can be in unit dosage form. In such form, the composition is divided into unit doses containing appropriate quantities of the active component(s). The unit dosage form can be a packaged preparation, the package containing discrete quantities of the preparations, for example, packeted tablets, capsules, and powders in vials or ampoules. The unit dosage form can also be a capsule, cachet, or tablet itself, or it can be the appropriate number of any of these packaged forms.

In certain embodiments, the vitamin D product is to be employed in the present compositions in a range of about 400 IU to about 10,000 IU per dosage form, preferably in the range of about 2,000 to about 8,000, more preferably in the range of about 3,000 to 7,000. Further, the compositions of the present invention may comprise from 0.01% to 25% by weight of the composition of the vitamin D product, preferably from about 0.1% to 20% by weight of the composition of the vitamin D product, more preferably from about 0.5% to 10% by weight of the composition of the vitamin D product. In another embodiment of the invention, the composition comprises the appropriate amount of dosages of the vitamin D product to account for the degradation, if any, of the vitamin D product.

In certain embodiments, the naltrexone product to be employed in the present compositions in a solid oral dosage form contains a therapeutically effective amount of naltrexone, which may be, for example, from about 0.01 mg to up to 50 mg, preferably from about 0.01 mg to about 40 mg, most preferably from about 0.01 to about 20 mg of the naltrexone product per tablet; e.g. about 0.01 mg, about 0.05 mg, about 0.1 mg, about 0.3 mg, about 0.5 mg, about 1 mg, about 2 mg, about 3 mg, about 5 mg, about 10 mg, about 20 mg, about 30 mg, about 40 mg or about 50 mg of the naltrexone product per tablet. In certain embodiments, the composition comprises the appropriate amount of dosages of the naltrexone product to account for degradation, if any, of the naltrexone product. In certain embodiments the composition comprises of from 3 mg to 4.5 mg.

In certain embodiments, the naltrexone product to be employed in the present compositions is selected from the list consisting of naltrexone, naloxone, methylnaltrexone or 6-β naltrexol, or a pharmaceutically acceptable salt thereof. Preferably, the naltrexone product is 6-β naltrexol or a pharmaceutically acceptable salt thereof.

The pharmaceutical composition may be provided as a blend of both the vitamin D product and the naltrexone product and a combination of pharmaceutically acceptable excipients. As used herein, the term "excipient" refers to a pharmaceutically acceptable ingredient that is commonly used in pharmaceutical technology for the preparation of solid oral dosage formulations. Examples of categories of excipients include, but are not limited to, binders, disintegrants, lubricants, glidants, stabilizers, fillers, and diluents. The amount of each excipient used may vary within ranges conventional in the art. The following references which are all hereby incorporated by reference disclose techniques and excipients used to formulate oral dosage forms. See The Handbook of Pharmaceutical Excipients, 4th edition, Rowe et al., Eds., American Pharmaceuticals Association (2003); and Remington: the Science and Practice of Pharmacy, 20th edition, Gennaro, Ed., Lippincott Williams & Wilkins (2000).

Suitable excipients include magnesium carbonate, magnesium stearate, talc, lactose, lactose monohydrate, sugar, pectin, dextrin, starch, tragacanth, microcrystalline cellulose, methyl cellulose, sodium carboxymethyl cellulose, corn starch, colloidal anhydrous Silica, titanium dioxide, a low-melting wax, cocoa butter, and the like.

In another embodiment, the pharmaceutical composition comprises at least one excipient.

In another embodiment, the pharmaceutical composition according to any embodiment of the second aspect of the invention is for use according to any embodiment of the first aspect of the invention. In another embodiment, the pharmaceutical composition is for use in the therapy of psoriasis, SLE or thyroiditis, preferably SLE or thyroiditis.

In a third aspect of the invention, there is provided a method for the treatment of an autoimmune disease comprising administering to a subject in need thereof, a therapeutically effective amount of naltrexone, or an analogue thereof, wherein the analogue is methylnaltrexone, naloxone, nalmefene and nalorphine, and vitamin D or an active metabolite or a pharmaceutically acceptable salt of either, wherein said naltrexone product and said vitamin D product are to be administered separately, sequentially or simultaneously.

In certain embodiments, the naltrexone product is selected from the list consisting of naltrexone, naloxone, methylnaltrexone or 6-β naltrexol. Preferably, the naltrexone product is 6-β naltrexol.

The term "therapeutically effective amount" is defined as an amount of naltrexone or an analogue thereof, wherein the analogue is methylnaltrexone, naloxone, nalmefene and nalorphine or a pharmaceutically acceptable salt of either, in combination with a vitamin D, or an active metabolite or a pharmaceutically acceptable salt of either, that preferably results in a decrease in severity of disease symptoms, an increase in frequency and duration of disease symptom-free periods, or a prevention of impairment or disability due to the disease affliction. The terms "effective amount" or "pharmaceutically effective amount" refer to a sufficient amount of an agent to provide the desired biological or therapeutic result. That result can be reduction, amelioration, palliation, lessening, delaying, and/or alleviation of one or more of the signs, symptoms, or causes of a disease, or any other desired alteration of a biological system. In reference to an autoimmune disease, an effective amount may comprise an amount sufficient to cause reduction in swelling, pruritus, fatigue, general malaise, fever, skin lesions, hair loss or weight loss. In some embodiments, an effective amount may result in halting the further progression of symptoms of the disorder or the emergence of symptoms of the disorder.

In some embodiments, a therapeutically effective amount is an amount sufficient to prevent or delay recurrence of symptoms of the autoimmune disease. A therapeutically effective amount can be administered in one or more administrations. For example, for the treatment of an autoimmune disease, a "therapeutically effective dosage" may induce a reduction in symptoms, for example, in the treatment of psoriasis, the reduction in the surface area of the skin of the subject inflamed as a result of the disease, by at least about 5% relative to baseline measurement, such as at least about 10%, or about 20%, or about 60% or more. The baseline measurement may be derived from the surface area of the skin subject to lesions, swelling and/or redness prior to administration of the treatment.

A therapeutically effective amount of a therapeutic preparation or preparations can decrease the severity of symptoms, or otherwise ameliorate symptoms in a subject. One of ordinary skill in the art would be able to determine such amounts based on such factors as the subject's size, the severity of the subject's symptoms, and the particular composition or route of administration selected.

In a fourth aspect of the invention, there is provided the use of naltrexone or an analogue thereof, wherein the analogue is methylnaltrexone, naloxone, nalmefene and nalorphine, in the manufacture of a medicament for the therapy of an autoimmune disease, wherein the medicament is to be administered to a subject in need of thereof simultaneously, separately or sequentially with vitamin D or an active metabolite, or a pharmaceutically acceptable salt of either.

In a fifth aspect of the invention, there is provided the use of vitamin D or an active metabolite in the manufacture of a medicament for the therapy of an autoimmune disease, wherein the medicament is to be administered to a subject in need of thereof simultaneously, separately or sequentially with naltrexone or an analogue thereof, wherein the analogue is methylnaltrexone, naloxone, nalmefene and nalorphine, or a pharmaceutically acceptable salt of either.

In further embodiments of both the third, fourth and fifth aspects of the invention, said method or said uses have the same optional and preferred features as are applicable to the first aspect of the invention.

EXAMPLES

Example 1-38 Year Old Female Patient With Hashimotos Thyroiditis, Fibromyalgia and Eosinophilic Esophagitis Treated With LDN and Vitamin D Patient's symptoms included severe fatigue and muscle aches and pains over her body from the fibromyalgia. She was already taking Vitamin D at a daily dosage of 5,000 units and 130 mg of Nature Throid supplementation (a porcine product). For the first week of LDN treatment, the patient was administered daily dosages of 1.5 mg LDN and the 5,000 units of Vitamin D continued. During the second week, the daily dosage of LDN was increased to 3.0 mg. During the third week, the daily dosage of LDN was increased to 4.5 mg. After a month of treatment the patient was subjected to the SpectraCell test (SpectraCell Laboratories, Inc. Dallas, Texas) to determine her Vitamin D levels, which were found to be severely deficient at a level of 47 (55 is adequate). Administration of Vitamin D was increased to 7,000 units per day. During treatment, the fibromyalgia symptoms gradually improved and almost entirely disappeared. Her thyroid levels remained high with a free T3 (triiodothyronine) range, which indicates an overactive thyroid gland, but her requirements for Nature Thyroid supplementation went down from 130 mg to 90 mg; unfortunately her reverse T3 (an inactive form of T3) maintains at a high level of about 42 which interferes at the cellular level blocking the receptor sites from the T3 activation. The overall reduction in thyroid dosage from 130 to 90 mg showed that the patient was maintaining good levels of thyroid physiology despite the high reverse T3, affiliated to the reduction of the antibody activity by naltrexone. Symptoms of eosinophilic esophagitis were significantly reduced.

In conclusion the patient was on vitamin D prior to naltrexone. When naltrexone was added and her vitamin D levels were raised, her disease states improved significantly. Her thyroid medication requirements were reduced. Her symptoms of fibromyalgia were resolved after addition of the naltrexone to the regimen.

Example 2-46 Year Old Female Patient With Thyroiditis Treated With LDN and Vitamin D The patient was receiving Synthroid as treatment for hypothyroidism, and she also presented with a rare form of macular degeneration requiring intra-ocular injections and interstitial cystitis. She started on a treatment regime of 5,000 units of Vitamin D per day, which she did not seem to have any significant effect in regards to her interstitial cystitis. At the time she was not aware she had autoimmune thyroiditis. While she was maintaining 5,000 units of vitamin D daily she had a vitamin D 25 OH level drawn which showed a deficient level of 39, measured by a standard serum test well-known in the art.

Upon diagnosis with thyroiditis the patient was treated with a porcine based thyroid. The thyroid peroxidase (TPO) levels give a measure of the antibody production levels which also relates to autoimmune activity. This antibody activity then can interfere with the ability to incorporate iodine into the thyroid molecule, thus interfering with thyroid cell function. TPO antibody values were obtained and found to be 176 iu/ml, which is unfavourably high. Naltrexone was added to her treatment regimen at a daily dosage of 1.5 mg per day for one week, which was then increased to 3.0 mg per day for a week and then increased to 4.5 mg per day. After treatment her TPO antibodies dropped from 176 iu/ml to 113 iu/ml. A subsequent measurement showed the level of TPO antibodies dropping to 67 iu/ml. Another subsequent measurement showed the level of TPO antibodies was 126 iu/ml. Also at the time her highly sensitive C Reactive Protein (CRP) was high at 4.3 and her thyroid stimulating hormone (TSH) was 0.0006.

Her dosage for Nature Throid was 97.5 mg twice a day for her thyroid supplementation. Her vitamin D level was 45 ng/ml, T3 was 4.1 and T4 (thyroxine, which converts into T3 in peripheral tissues) was 0.84. Her thyroid has stabilized as shown by these values; the patient's levels are at optimal levels where the T3 is in the upper range. It also shows since the T4 is at the lower range and T3 is at the upper range is she is converting T4 to T3 efficiently.

In conclusion, the combination of LDN and Vitamin D significantly helped the treatment of the thyroiditis and saw a significant reduction in the patient's symptoms and sufferings.

Example 3-54 Year Old Female Patient With Systemic Lupus Erythematosis (SLE) and Sjorgren's Disease Patient's symptoms were dry skin, mouth and eyes from the Sjogren's. Her SLE symptoms were joint pain, swelling, overall body pain, and extreme, almost debilitating, fatigue. She was treated with plaquenil 200 mg twice a day with minimal benefit. Subsequently, she was treated with a daily dosage of 3.0 mg of naltrexone titrating up to 4.5 mg per day over 4 weeks. She was also started empirically on Vitamin D3 5,000 units per day.

She was also prescribed Dehydroepiandrosterone (DHEA) 5 mg and Nature Throid thyroid hormone supplement 48.75 mg, progesterone 100 mg every night and testosterone cream 4 mg per day for low libido, and she was taking turmeric and krill oil. She started tapering off the plaquenil.

During treatment estradiol 1.0 mg was started and also at this point she was off the plaquenil for 3 weeks totally. Her hand stiffness and pain had improved significantly about 60% reduction in pain level. Standard laboratory serum tests well-known in the art showed an erythrocyte sedimentation rate of 2.0 (0-20), which demonstrates no inflammation was present, and that the high sensitive CRP was 0.8 (0-3.0), which also did not show any inflammation. In addition, her Free T3 (triiodothyronine) was 3.1.

During the treatment regimen, the administered DHEA was increased to 10 mg. The DHEA hormone was measured to be 203, Estradiol 117, progesterone 0.2, T3 3.3. Later measurements showed the DHEA was 142, Estradiol 141, total testosterone 19, Free testosterone 1.3, highly sensitive C Reactive protein was up slightly at 1.76 (0-3.0), Her laboratory results showed T3 4.1, T4 0.97, Reverse T3 19.7, Estradiol 46, DHEA 169. The patient's levels are at optimal levels where the T3 is in the upper range. It also shows since the T4 is at the lower range and T3 is at the upper range is she is converting T4 to T3 efficiently.

In conclusion, her clinical symptoms have improved dramatically; in addition her inflammatory markers have remained in the normal range during the time she has been treated with 5,000 iu of vitamin D3 and 4.5 mg of naltrexone. The improvement in her pain has been about 60% reduction in pain and she does not have any more joint swelling. She has been able to stop the traditional immunosuppressant plaquenil. Low dose naltrexone and Vitamin D3 had a much better effect on her symptoms than the plaquenil.

The invention claimed is:

1. A method of treating an autoimmune disease comprising administering simultaneously naltrexone or a pharmaceutically acceptable salt thereof, and vitamin D or a pharmaceutically acceptable salt thereof, wherein the autoimmune disease is psoriasis, Systemic Lupus Erythematosus (SLE) or thyroiditis, wherein the naltrexone or pharmaceutically acceptable salt thereof is administered at a dose less than 0.5 mg/kg.

2. The method of claim 1, wherein vitamin D or pharmaceutical salt is administered to the subject in an amount sufficient to bring the subject's blood vitamin D concentration to within a range of from 40 to 120 ng/ml.

3. The method of claim 1, wherein the naltrexone and the vitamin D product are provided as a combined preparation.

4. The method of claim 1, wherein the autoimmune disease is Systemic Lupus Erythematosis (SLE) or thyroiditis.

5. A method for the treatment of an autoimmune disease, comprising administering a subject in need thereof, a therapeutically effective amount of naltrexone or a pharmaceutically acceptable salt thereof, and vitamin D or a pharmaceutically acceptable salt thereof, wherein said naltrexone or pharmaceutically acceptable salt thereof and said vitamin D or pharmaceutically acceptable salt thereof are administered simultaneously, wherein the autoimmune disease is psoriasis, Systemic Lupus Erythematosus (SLE) or thyroiditis, wherein the naltrexone or pharmaceutically acceptable salt thereof is administered at a dose less than 0.5 mg/kg.

\* \* \* \* \*